US012089840B2

(12) United States Patent
Ayub

(10) Patent No.: US 12,089,840 B2
(45) Date of Patent: Sep. 17, 2024

(54) MEDICAL STAPLER FOR EFFICIENT SKIN AND TISSUE CLOSURE

(71) Applicant: Hamid Ayub, Plantation, FL (US)

(72) Inventor: Hamid Ayub, Plantation, FL (US)

(*) Notice: Subject to any disclaimer, the term of this patent is extended or adjusted under 35 U.S.C. 154(b) by 0 days.

(21) Appl. No.: 18/438,478

(22) Filed: Feb. 11, 2024

(65) Prior Publication Data
US 2024/0180550 A1 Jun. 6, 2024

(51) Int. Cl.
A61B 17/068 (2006.01)
A61B 17/064 (2006.01)
A61B 17/00 (2006.01)
A61B 17/072 (2006.01)

(52) U.S. Cl.
CPC ...... *A61B 17/0684* (2013.01); *A61B 17/0644* (2013.01); *A61B 2017/00376* (2013.01); *A61B 2017/07228* (2013.01); *A61B 2017/07235* (2013.01); *A61B 2017/07242* (2013.01); *A61B 2017/07278* (2013.01)

(58) Field of Classification Search
CPC ... A61B 17/068; A61B 17/064; B25C 5/1603; B25C 5/025
See application file for complete search history.

(56) References Cited

U.S. PATENT DOCUMENTS

| | | | | |
|---|---|---|---|---|
| 4,556,161 A | * | 12/1985 | Oide | B25C 5/025 227/120 |
| 5,931,364 A | * | 8/1999 | Dennis | B25C 7/00 227/120 |
| 5,931,365 A | * | 8/1999 | Huang | B25C 5/1679 227/139 |
| 6,076,720 A | * | 6/2000 | Deng | B25C 5/1603 227/123 |
| 7,059,509 B2 | * | 6/2006 | Brown | A61B 17/0684 227/176.1 |

* cited by examiner

*Primary Examiner* — Nathaniel C Chukwurah

(57) ABSTRACT

The present disclosure provides a medical stapler that comprises an assembly of staples to close an incision. The assembly of staples comprises of one or more standard staples and one or more fine staples. Further, the medical stapler comprises a first staple track and a second staple track. The first staple track is configured to hold the one or more standard staples. The second staple track is configured to hold the one or more fine staples. Further, the medical stapler comprises one or more hammers/anvils arranged over the assembly of staples for dispensing and puncturing the one or more standard staples and the one or more fine staples to close the incision.

10 Claims, 8 Drawing Sheets

MEDICAL STAPLER FOR EFFICIENT SKIN AND TISSUE CLOSURE

FIELD OF INVENTION

Embodiments of a present disclosure relate to the field of surgical instruments and more particularly to a surgical stapler for approximation of skin and deeper tissues.

BACKGROUND

A wound closure is managed through a fundamental approach which involves application of multiple simple sutures or vertical mattress sutures. In vertical mattress sutures, the same sutures which brings deep tissue together, bring skin edges together also. It results in aesthetically pleasant scar when incision or wound healing is complete.

Further, in certain surgical scenarios, the conventional method of using sutures with a needle and thread becomes impractical. There are instances, where a faster method of closure becomes imperative and prolonged anaesthesia introduces an increased risk of complications for a patient. Thus, expedited closure methods become essential in circumstances where can reduce the duration of anaesthesia is critical to mitigate potential risks and enhance patient safety.

Moreover, a surgical stapler addresses these challenges as a specialized surgical instrument designed for the swift and efficient closure of incisions or wounds during various surgical procedures. The surgical stapler functions by deploying different size metal staples to secure tissues together, providing an alternative to traditional sutures. The surgical staples find common use across various surgical disciplines, for approximation of any incision or wound.

Despite the effectiveness of conventional surgical staples in promptly closing wounds and incisions, certain limitations are associated with their use. A notable drawback is the potential for the resulting scar to be visible and aesthetically displeasing. The linear pattern of staples can, at times, lead to a more noticeable scar, especially in areas where cosmetic outcomes are of primary concern.

To address the concerns in the background, an effective way for wound closures is required. A surgical stapler with different sized pins is proposed in this disclosure.

SUMMARY

This summary is provided to introduce a selection of concepts, in a simple manner, which is further described in the detailed description of the disclosure. This summary is neither intended to identify key or essential inventive concepts of the subject matter nor to determine the scope of the disclosure.

A medical stapler for suture, where the medical stapler comprising an assembly of staples to close an incision. The assembly of staples comprises of one or more standard staples and one or more fine staples; a first staple track and a second staple track, wherein the first staple track is configured to hold the one or more standard staples, wherein the second staple track is configured to hold the one or more fine staples and one or more hammers/anvils arranged over the assembly of staples for dispensing and puncturing the one or more standard staples and the one or more fine staples to close the incision.

The large staples bring deeper tissues together. The small and finer staples bring skin edges together, to have similar to vertical mattress fashion with staples.

The terms "Larger Staple", "Smaller Staple", "Standard Staple" and "Fine Staple" are used interchangeably in the document. The terms "Larger Staple" is similar to "Standard Staple" and "Smaller Staple" is similar to "Fine Staple" and same is for the staple pins.

To further clarify the advantages and features of the present disclosure, a more particular description of the disclosure will follow by reference to specific embodiments thereof, which are illustrated in the appended figures. It is to be appreciated that these figures depict only typical embodiments of the disclosure and are therefore not to be considered limiting in scope. The disclosure will be described and explained with additional specificity and detail with the appended figures.

BRIEF DESCRIPTION OF DRAWINGS

The disclosure will be described and explained with additional specificity and detail with the accompanying figures in which.

Figure 1:
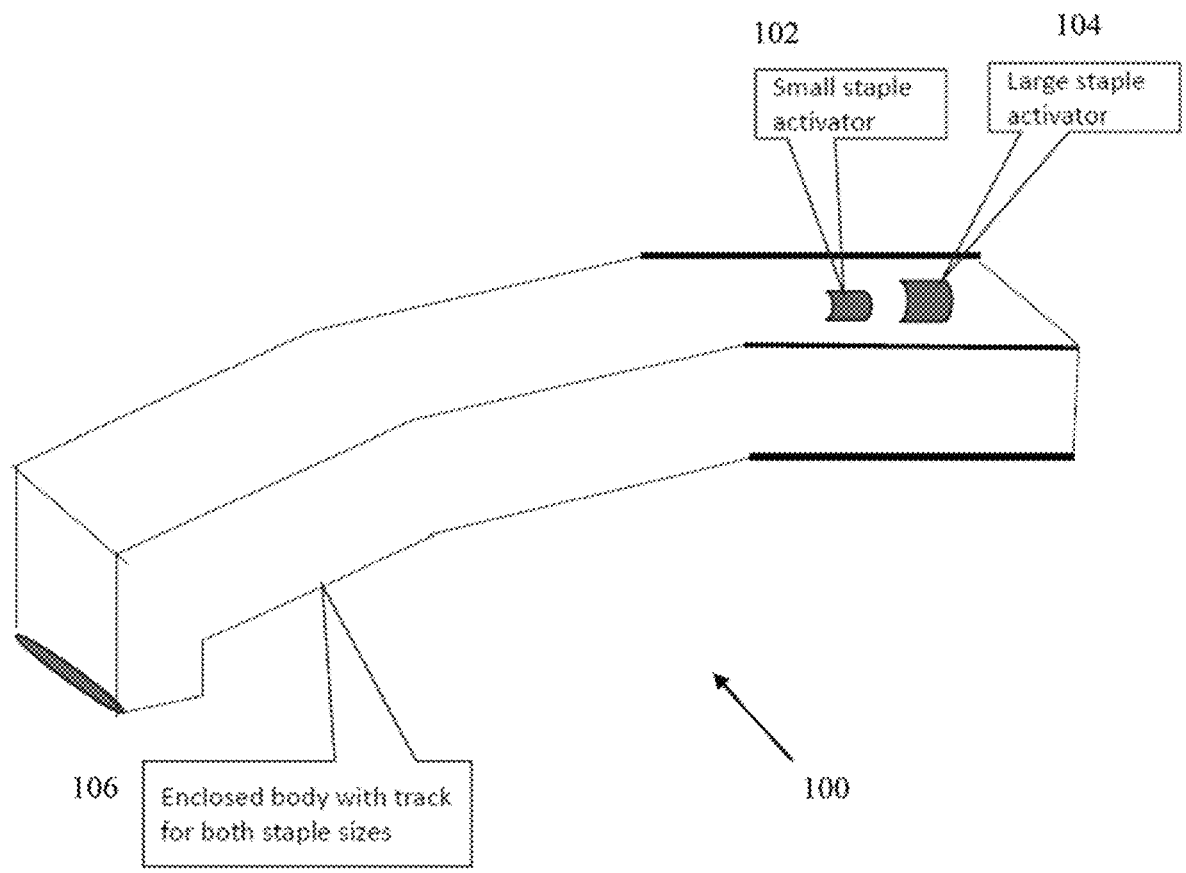
FIG. 1A is a schematic diagram illustrating a medical stapler design in accordance with embodiment of the present disclosure.
FIG. 1B is a perspective diagram illustrating a medical stapler design with Multi-Track Configuration in accordance with embodiment of the present disclosure.
FIG. 1C is perspective diagram illustrating the arrangement of assembly of staples and the one or more anvils, in accordance with embodiment of the present disclosure.
FIG. 1D is perspective diagram illustrates the assembly of staples in the medical stapler, as described in accordance with an embodiment of the present disclosure.
Figure 1:
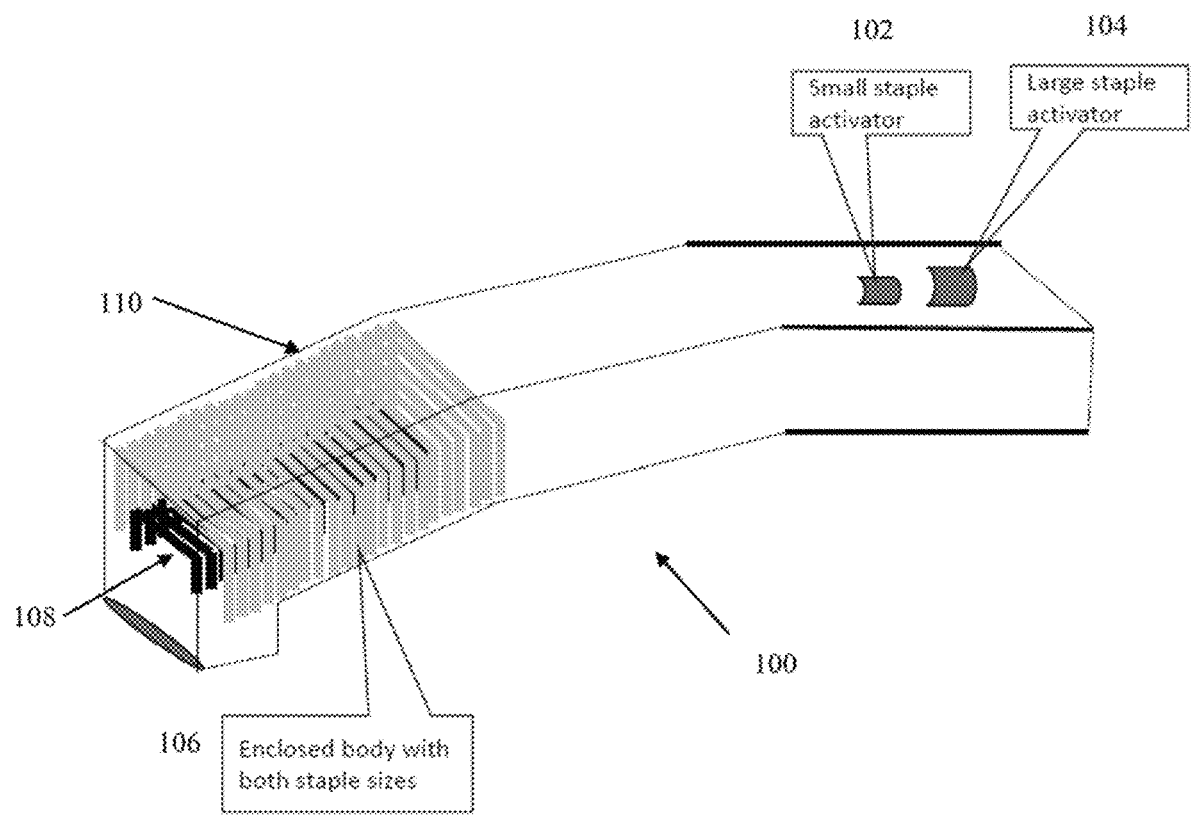
Figure 1:
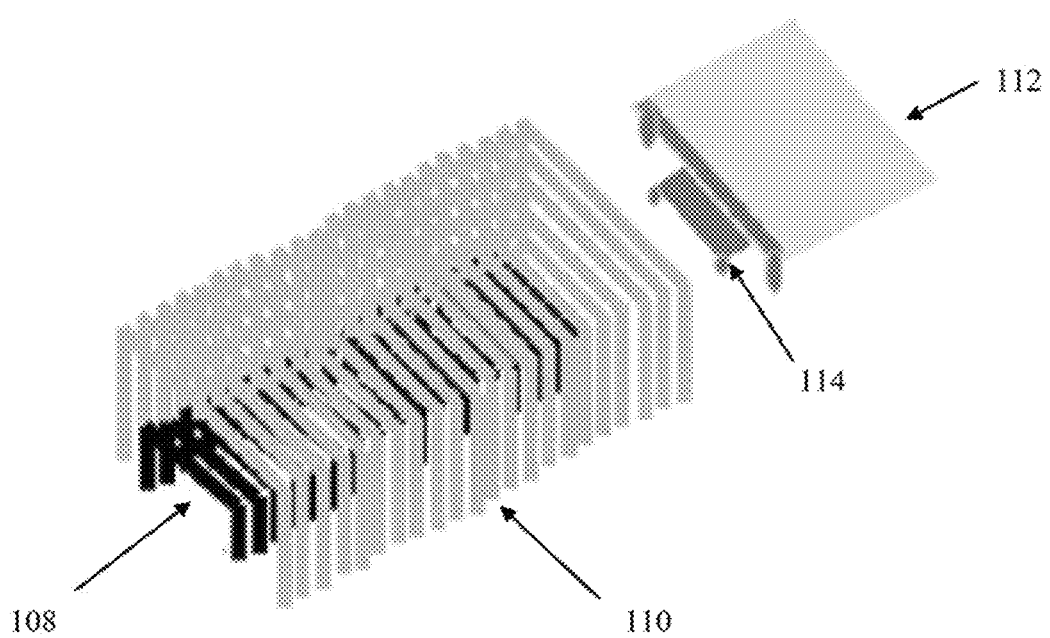
Figure 1:
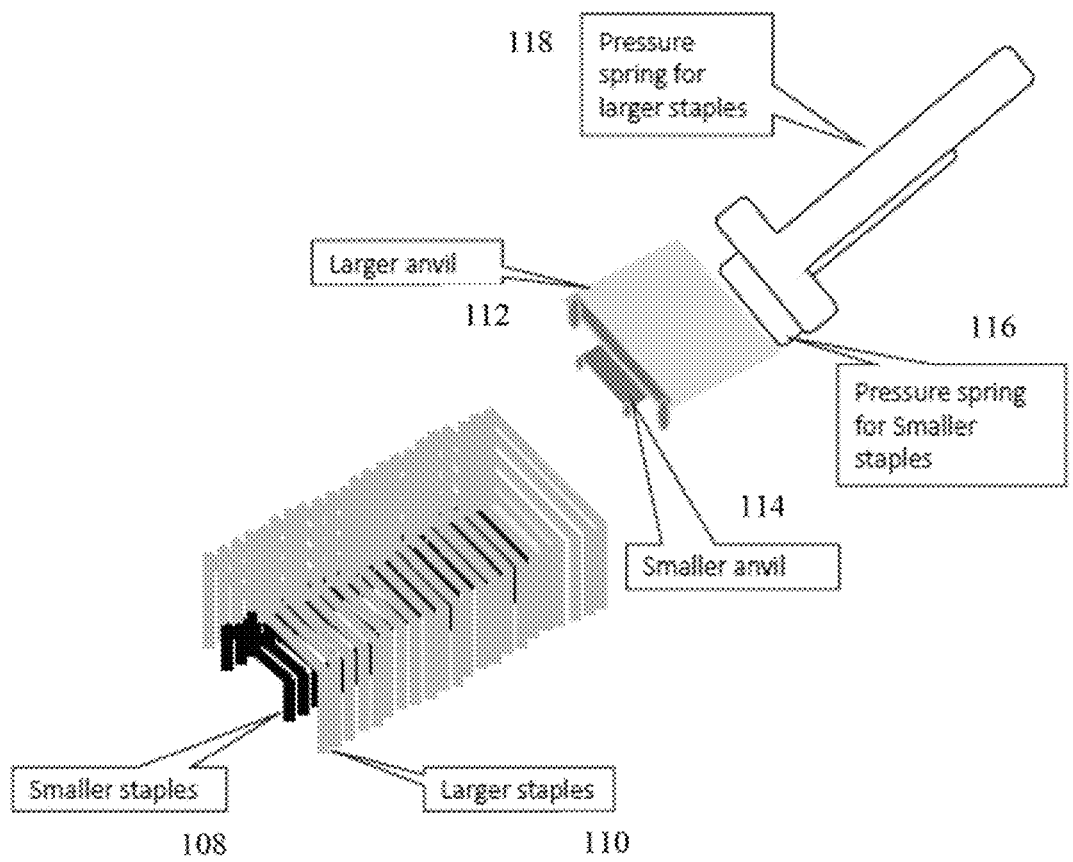

Further, those skilled in the art will appreciate that elements in the figures are illustrated for simplicity and may not have necessarily been drawn to scale. Furthermore, in terms of the construction of the device, one or more components of the device may have been represented in the figures by conventional symbols, and the figures may show only those specific details that are pertinent to understanding the embodiments of the present disclosure so as not to obscure the figures with details that will be readily apparent to those skilled in the art having the benefit of the description herein.

DETAILED DESCRIPTION OF THE DISCLOSURE

For the purpose of promoting an understanding of the principles of the disclosure, reference will now be made to the embodiment illustrated in the figures and specific language will be used to describe them. It will nevertheless be understood that no limitation of the scope of the disclosure is thereby intended. Such alterations and further modifications in the illustrated system, and such further applications of the principles of the disclosure as would normally occur to those skilled in the art are to be construed as being within the scope of the present disclosure. It will be understood by those skilled in the art that the foregoing general description and the following detailed description are exemplary and explanatory of the disclosure and are not intended to be restrictive thereof.

In the present document, the word "exemplary" is used herein to mean "serving as an example, instance, or illustration." Any embodiment or implementation of the present subject matter described herein as "exemplary" is not necessarily to be construed as preferred or advantageous over other embodiments.

The terms "comprise", "comprising", or any other variations thereof, are intended to cover a non-exclusive inclusion, such that one or more devices or sub-systems or elements or structures or components preceded by "comprises . . . a" does not, without more constraints, preclude the existence of other devices, sub-systems, additional sub-modules. Appearances of the phrase "in an embodiment", "in another embodiment" and similar language throughout this specification may, but not necessarily do, all refer to the same embodiment.

Unless otherwise defined, all technical and scientific terms used herein have the same meaning as commonly understood by those skilled in the art to which this disclosure belongs. The system, methods, and examples provided herein are only illustrative and not intended to be limiting.

The described medical stapler is designed for suturing purposes, featuring an assembly of both standard and fine staples. The stapler includes two separate tracks for these staples—the first track holds standard staples, and the second track holds fine staples. Additionally, the stapler incorporates hammers/anvils to dispense and puncture the staples, facilitating the closure of incisions. This design allows for versatile and precise closure, accommodating different tissue layers efficiently. The stapler's ability to use various staples in distinct tracks, along with the targeted dispensing mechanism, offers a flexible and effective solution for surgical procedures, promoting improved closure outcomes.

FIG. 1A is a schematic diagram illustrating a medical stapler (100) design in accordance with embodiment of the present disclosure. A small (102) and large staple activators (104) serve as intuitive user interfaces for deploying fine and standard staples, respectively. Nestled within the enclosed body, these activators govern separate tracks for each staple size, providing a sophisticated yet user-friendly medical stapler that allows for precise control and adaptability in staple selection during diverse medical procedures.

Small Staple Activator (102): The small staple activator is a crucial component within the medical stapler, meticulously crafted for the deployment of small or fine staples. This user-friendly interface, often presented as a button, allows the user to engage and initiate the deployment of smaller staples within the assembly. Its primary responsibility lies in controlling the mechanism that dispenses and punctures one or more fine staples, effectively facilitating the closure of the incision with precision.

Large Staple Activator (104): In parallel, the large staple activator stands as another integral component of the medical stapler, strategically designed to handle the deployment of larger or standard staples. Mirroring the functionality of the small staple activator, this interface provides a straightforward button for users to engage, initiating the deployment of larger staples within the assembly. The activator takes charge of controlling the mechanism responsible for dispensing and puncturing one or more standard staples, ensuring the effective closure of the incision.

Enclosed Body with Track for Both Staple Sizes (106): The enclosed body of the medical stapler serves as the primary structural framework that encapsulates essential components crucial to the stapling mechanism. This robust casing houses the staple assembly, hammers/anvils, and the activators, providing a secure environment for the seamless operation of the medical stapler. Within this enclosed body, a thoughtful design incorporates separate tracks dedicated to accommodating both small or fine staples and large or standard staples. The track associated with the small staple activator securely holds the one or more fine staples, while the track linked to the large staple activator cradles the one or more standard staples. This enclosed body acts as a protective casing, ensuring the proper alignment and functioning of internal components during the stapling process.

FIG. 1B is a perspective diagram illustrating a medical stapler design with Multi-Track Configuration in accordance with embodiment of the present disclosure. The enclosed body (106) of the medical stapler functions as the primary structural framework, housing essential components such as the staple assembly, hammers/anvils, and the activators. Contained within this structure are distinct tracks designed to accommodate both small or fine staples (108) and large or standard staples (110). These tracks can be configured either in a stacked arrangement or positioned side by side, offering versatility to meet various user preferences and surgical needs. Further the tracks can be arranged in any other arrangement. The track aligned with the small staple activator is dedicated to securing one or more fine staples, ensuring their precise deployment during the stapling process. Conversely, the track associated with the large staple activator is tailored for holding one or more standard staples, facilitating controlled release and effective puncturing to close the incision.

FIG. 1C is perspective diagram illustrating the arrangement of assembly of staples and the one or more anvils, in accordance with embodiment of the present disclosure. By incorporating both larger and smaller anvils, the medical stapler provides a versatile solution that caters to different staple sizes. This dual-anvil design enhances the stapler's adaptability, allowing healthcare professionals to choose the appropriate staple size based on the specific demands of the surgical procedure at hand.

Larger Staples (110) with Larger Anvil (112): The design includes a specific configuration for larger staples, complemented by a correspondingly larger anvil. This setup ensures that the stapler can effectively accommodate and deploy larger or standard-sized staples during the surgical procedure. The larger anvil is strategically designed to provide optimal support and surface area for the larger staples, promoting secure fastening and stability when closing incisions of a certain size.

Small Staples ((108)) with Small Anvil (114): In contrast, the medical stapler is equipped to handle smaller or fine staples with a dedicated small anvil. This component is tailored to the size and specifications of the smaller staples, offering precise support during deployment. The small anvil ensures accurate alignment and controlled puncturing for the finer staples, contributing to the versatility of the medical stapler in addressing various incision sizes and surgical requirements.

The schematic diagram in FIG. 1D illustrates the assembly of staples in the medical stapler, as described in accordance with an embodiment of the present disclosure. In this embodiment, the medical stapler (denoted as 100) is equipped with features for closing incisions using both standard or larger staples (110) and fine or smaller staples ((108)), complemented by an enhanced mechanism involving pressure springs tailored for each staple size. The assembly of staples is structured within the medical stapler 100, consisting of the one or more standard staples (110) and the one or more fine staples (108).

To optimize staple deployment, the medical stapler 100 incorporates a first staple track and a second staple track. The first staple track is specifically designed to house the one or more standard staples (110), while the second staple track is configured to secure the one or more fine staples (108). This dual-track system ensures precise control over the deployment of staples of varying sizes. For effective closure of the incision, the medical stapler 100 introduces one or more hammers/anvils arranged strategically over the staple assembly. These hammers/anvils are responsible for dispensing and puncturing both the standard staples (110) and the fine staples (108), ensuring a secure closure. A separator is also integrated to facilitate the separation of standard staples and fine staples during the stapling process. In addition to these features, the medical stapler 100 incorporates pressure springs dedicated to each staple size. A pressure spring for large staples (118) is incorporated to optimize the deployment of the one or more standard staples (110), while a separate pressure spring for small staples (116) is implemented to enhance the deployment of the one or more fine staples (108). These pressure springs contribute to the controlled and efficient operation of the stapler, ensuring consistent and reliable staple deployment during medical procedures. Furthermore, the medical stapler 100 includes distinct large and small hammers/anvils (112 and 114, respectively). The large hammer/anvil (112) facilitates the insertion of the one or more standard staples (110) into the skin, while the small hammer/anvil (114) guides the one or more fine staples (108) into the skin.

The medical stapler (100) is for vertical mattress suture and the medical stapler (100) also allows a medical practitioner to mimic a same effect of the vertical mattress suture technique for one or more deep and shallow sutures.

According to an exemplary embodiment, the one or more standard staples (110) and the one or more fine staples (108) are arranged in one or more ways which include an alternating order, or the one or more standard staples (110) followed by the one or more fine staple (108), or the one or more standard staples (110) and the one or more fine staples (108) are organized according to length, in which one or more staples of one length may be followed by one or more staples of the other length, one or more of one length of staple is followed by one or more of the other lengths of staple followed by one or more of the first length of staple.

According to an exemplary embodiment, the one or more standard staples (110) are applied first to close the deep and shallow sutures, followed by application of the one or more fine staples (108) to close one or more upper layers of tissue (e.g., skin) in a cosmetically appealing manner. In an alternate embodiment, the one or more standard staples (110) and the one or more fine staples (108) are applied in an alternating format where one or more standard staples (110) are applied, followed by one or more fine staples (108), followed by one or more long staples, etc.

The one or more standard staples (110) and the one or more fine staples 108 are made of one or more materials, wherein the one or more materials comprise at least one of titanium, stainless steel, or synthetic, bioabsorbable materials.

Further, the one or more standard staples (110) have length in a range from 8 to 12 mm and width in a range from 8 to 12 mm. The one or more standard staples (110) are punctured by the large hammer/anvil (112) into one or more tissues to close the incision with a depth ranging from 3 to 6 mm. In addition to this, the one or more fine staples (108) have length and width in a range from 3 to 6 mm. The one or more fine staples (108) are punctured by the small hammer/anvil (114) to close the incision at a superficial skin level with depth in a range from 1 to 3 mm.

Further, one or more hammers/anvils dispense and close the one or more standard staples (110) and one or more fine staples 108 at different locations, such that the medical stapler (100) is repositioned to deliver the one or more standard staples (110) with respect to the one or more fine staples (108). Additionally, the one or more hammers/anvils dispense and close the one or more standard staples (110) and the one or more fine staples 108 at same location for eliminating a need to reposition the medical stapler (100) to deliver the one or more standard staples 110 with respect to the one or more fine staples (108).

Further, the separator is for splitting the one or more standard staples (110) and the one or more fine staples 108. The separator assists in proper deployment of the one or more standard staples (110) and the one or more fine staples 108 to prevent any overlap or entanglement between the one or more standard staples (110) and the one or more fine staples 108, thereby facilitating a smooth and precise closure of the incision.

Figure 2:
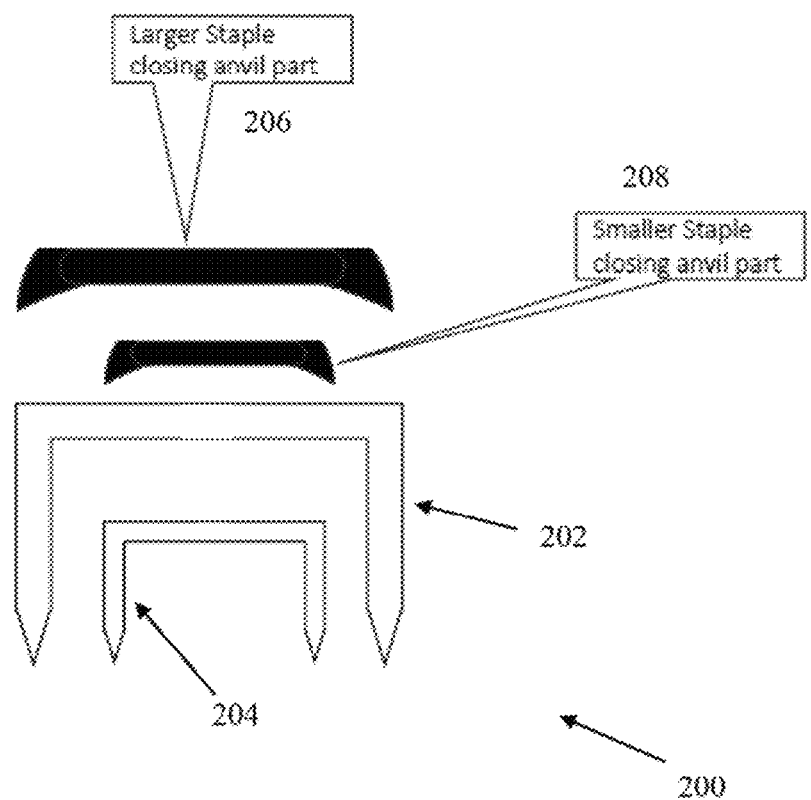
FIG. 2 illustrates a small and large staple closing anvil part, in accordance with embodiment of the present disclosure.

FIG. 2 illustrates a small and large staple closing anvil part, in accordance with embodiment of the present disclosure. The schematic diagram in reveals the intricate design of the medical stapler (denoted as 200) in accordance with the present disclosure. This embodiment incorporates a dual-track system, accommodating one or more standard staples (202) and one or more fine staples (204). The stapler features specialized hammers/anvils, including a large hammer/anvil (206) and a small hammer/anvil (208), strategically arranged to dispense and puncture both standard and fine staples for effective incision closure. Notably, the stapler's closing anvil mechanism is meticulously tailored with both small and large anvils, ensuring precision in guiding fine staples into the skin (via the small anvil) and facilitating the insertion of standard staples (via the large anvil). This comprehensive approach underscores the stapler's versatility, allowing for precise and controlled closure of incisions with staples of varying sizes.

Figure 3:
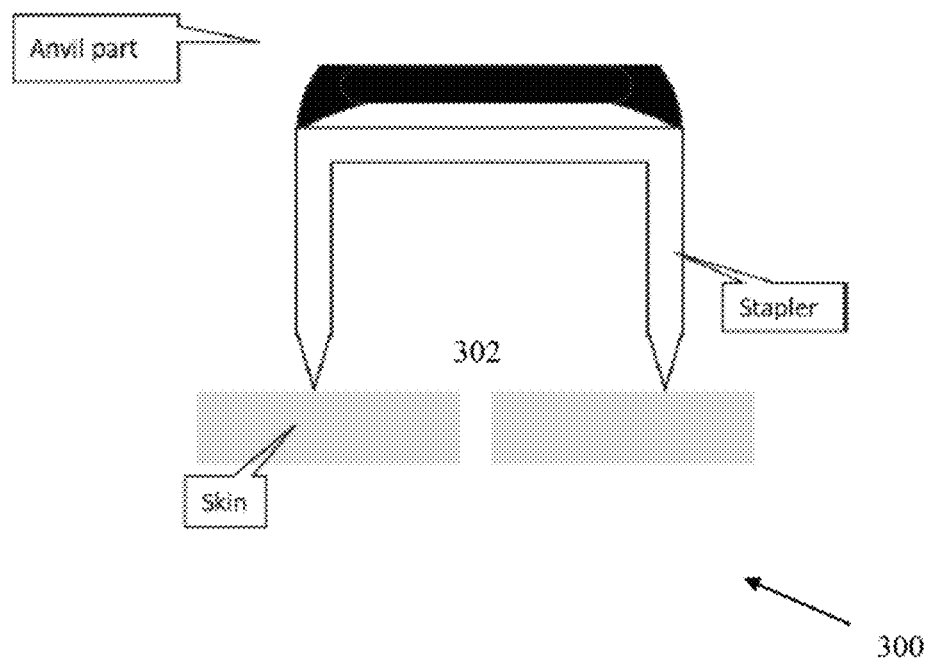
FIGS. 3A-3C are perspective diagrams illustrating the insertion of the assembly of staples into skin of a patient to close the incision, in accordance with embodiment of the present disclosure.
Figure 3:
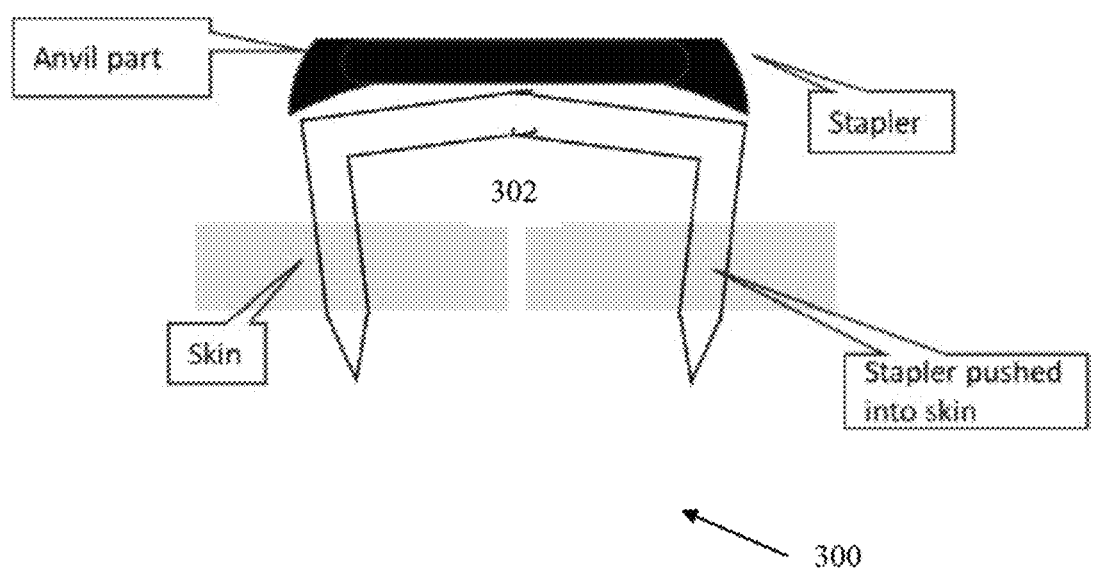
Figure 3:
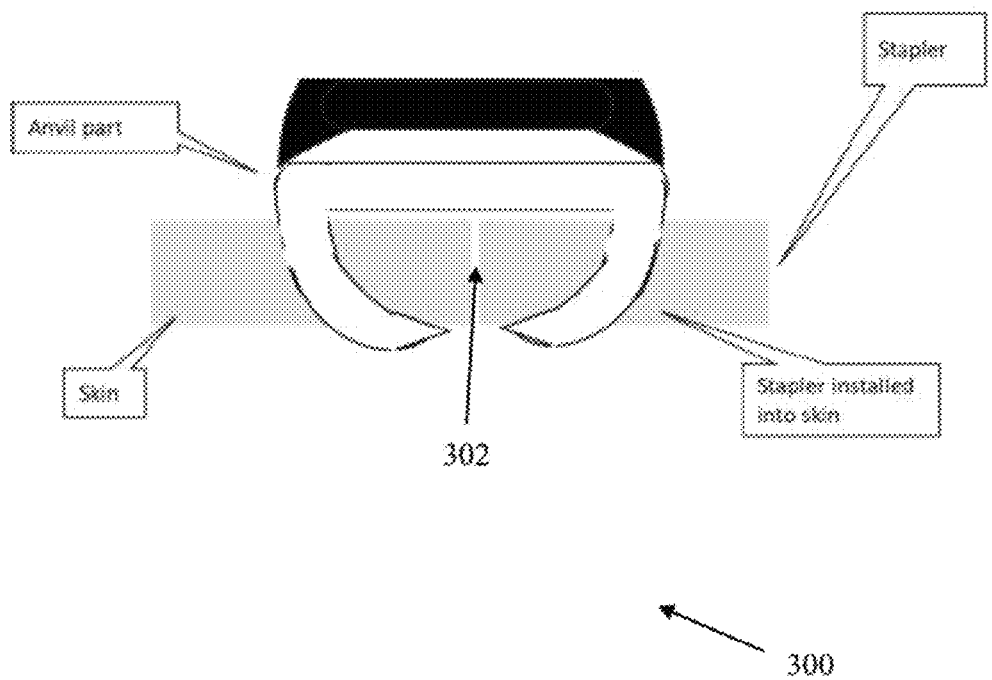

FIG. 3A-3C are perspective diagrams (300) illustrating the insertion of the assembly of staples into skin of a patient to close the incision (302), in accordance with embodiment of the present disclosure. According to FIG. 3A, the assembly of staples are positioned over a targeted incision (302) and the one or more hammers/anvils are aligned above the assembly of staple. According to FIG. 3B, the assembly of staples are pushed into the skin via the one or more hammers/anvils. According to FIG. 3C, the assembly of staples are inserted into the skin for closing the incision (302).

For instance, when the medical practitioner performs an abdominal surgery, where there is a requirement of closure of both one or more deep tissue layers and the superficial skin, the medical practitioner uses the one or more standard staples (110) to secure the one or more deep tissue layers and penetrating through an abdominal wall. Following this, the medical practitioner may seamlessly switch to the one or more fine staples 108, without the need to reposition the medical stapler (100). Further, the alternating arrangement or sequential application of the one or more standard staples (110) and the one or more fine staples 108 ensures a comprehensive closure. The larger hammer/anvil (112) accommodates the one or more standard staples (110) for the one or more deep tissue layers, while the small hammer/anvil (114) facilitates the application of the one or more fine staples (108) for superficial skin closure and this flexible approach not only expedites the closure process but also enhances the cosmetic outcome, minimizing the risk of visible scar. The medical stapler 100 thus provides a versatile solution for various surgical scenarios, allowing practitioners to adapt the approach based on the specific requirements of each case.

Thus, various embodiments of the present disclosure provide medical stapler 100 for suture. The medical stapler (100) improves the ability of medical practitioner to close the incision in a much shorter time period while reducing the chances of a scar. Further, the medical stapler delivers the one or more standard staples (110) and one or more fine staples 108 for closing the incision, wherein the one or more standard staples (110) are utilized to close the one or more deep layers of tissue by puncturing deeper into the tissue to close the incision. The one or more fine staples (108) are used to close the incision at the superficial skin level by puncturing the superficial layers of the tissue surrounding the incision with the one or more fine staples (108) to bring together one or more upper layers of tissue (e.g., skin) in a cosmetically appealing manner.

The advantages of the described medical stapler invention include:
1) Versatile Closure: The stapler offers a versatile solution for closure, accommodating both standard and fine staples. This versatility allows for effective closure of different layers, addressing both deeper tissues and skin edges.
2) Precision in Closure: The separate tracks for standard and fine staples, along with the hammers/anvils, enable precise and controlled placement of staples, ensuring accurate closure of the incision.
3) Efficiency in Tissue Closure: The use of large staples for deeper tissues and smaller, finer staples for skin edges enhances the efficiency of tissue closure. This approach allows for tailored closure based on the specific needs of different layers.
4) Elimination of Knots: By utilizing staples instead of traditional sutures, the invention eliminates the need for knots. This simplifies the closure process and reduces the potential complications associated with knot tying.
5) Consistent Vertical Mattress Fashion: The invention achieves a closure pattern similar to a vertical mattress fashion with staples, promoting a secure and reliable closure method
6) Reduced Procedure Time: The design of the stapler, with its dual tracks and targeted staple application, may contribute to a reduction in overall procedure time compared to traditional closure methods.
7) Enhanced Healing: The precise and efficient closure facilitated by the stapler can contribute to improved wound healing outcomes for patients.
8) Ease of Use: The stapler's design allows for straightforward operation, making it user-friendly for medical professionals performing closures.

The illustrated steps are set out to explain the exemplary embodiments shown, and it should be anticipated that ongoing technological development will change the manner in which particular functions are performed. These examples are presented herein for purposes of illustration, and not limitation. Further, the boundaries of the functional building blocks have been arbitrarily defined herein for the convenience of the description. Alternative boundaries can be defined so long as the specified functions and relationships thereof are appropriately performed. Alternatives (including equivalents, extensions, variations, deviations, etc., of those described herein) will be apparent to persons skilled in the relevant art(s) based on the teachings contained herein. Such alternatives fall within the scope and spirit of the disclosed embodiments. Also, the words "comprising," "having," "containing," and "including," and other similar forms are intended to be equivalent in meaning and be open-ended in that an item or items following any one of these words is not meant to be an exhaustive listing of such item or items or meant to be limited to only the listed item or items. It must also be noted that as used herein and in the appended claims, the singular forms "a," "an," and "the" include plural references unless the context clearly dictates otherwise.

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based here on. Accordingly, the embodiments of the present disclosure are intended to be illustrative, but not limiting, of the scope of the invention, which is set forth in the following claims.

What is claimed is:
1. A medical stapler for suture, the medical stapler comprising:
   an assembly of staples to close an incision, wherein the assembly of staples comprises of one or more standard staples and one or more fine staples;
   a first staple track and a second staple track, wherein the first staple track is configured to hold the one or more standard staples, wherein the second staple track is configured to hold the one or more fine staples;
   one or more hammers/anvils arranged over the assembly of staples for dispensing and puncturing the one or more standard staples and the one or more fine staples to close the incision; and
   wherein the medical stapler further comprises one or more hammers/anvils for closing the incision, wherein the one or more hammers/anvils comprise a large hammer/anvil and a small hammer/anvil.

2. The medical stapler of claim 1, wherein the medical stapler designed specifically for vertical mattress suture fashion, excluding the use of knots and emphasizing the impact of bringing the skin together at two distinct spots.

3. The medical stapler of claim 1, wherein the one or more standard staples and the one or more fine staples are arranged in one of an alternating order or the one or more standard staples followed by the one or more fine staples.

4. The medical stapler of claim 1, wherein the one or more standard staples and the one or more fine staples are made of one or more materials, wherein the one or more materials comprise at least one of titanium, stainless steel, or synthetic, bioabsorbable materials.

5. The medical stapler of claim 1, wherein the one or more standard staples have length in a range from 8 to 12 mm and width in a range from 8 to 12 mm.

6. The medical stapler of claim 1, wherein the one or more fine staples have length and width in a range from 3 to 6 mm.

7. The medical stapler of claim 1, wherein the one or more standard staples are punctured by the one or more hammers/anvils into one or more tissues to close the incision with a depth ranging from 3 to 6 mm.

8. The medical stapler of claim 1, wherein the one or more fine staples are punctured by the one or more hammers/anvils to close the incision at a superficial skin level with depth in a range from 1 to 3 mm.

9. The medical stapler of claim 1, wherein the one or more hammers/anvils dispense and close the one or more standard staples and one or more fine staples at different locations, such that the medical stapler is repositioned to deliver the one or more standard staples with respect to the one or more fine staples.

10. The medical stapler of claim 1, wherein the one or more hammers/anvils dispense and close the one or more standard staples and the one or more fine staples at same location for eliminating a need to reposition the medical stapler to deliver the one or more standard staples with respect to the one or more fine staples.

* * * * *